US010737076B2

(12) United States Patent
Boden, Jr. et al.

(10) Patent No.: US 10,737,076 B2
(45) Date of Patent: Aug. 11, 2020

(54) SELF-OFFSETTING IMPLANTABLE CATHETER SYSTEM

(71) Applicant: Integra LifeSciences Switzerland Sárl, Le Locle (CH)

(72) Inventors: Thomas Boden, Jr., Middleboro, MA (US); Alan J. Dextradeur, Franklin, MA (US)

(73) Assignee: Integra LifeSciences Switzerland Sárl, Le Locle (CH)

( * ) Notice: Subject to any disclaimer, the term of this patent is extended or adjusted under 35 U.S.C. 154(b) by 330 days.

(21) Appl. No.: 15/386,848

(22) Filed: Dec. 21, 2016

(65) Prior Publication Data
US 2018/0169394 A1 Jun. 21, 2018

(51) Int. Cl.
*A61M 27/00* (2006.01)
*A61M 25/00* (2006.01)
*A61M 25/04* (2006.01)

(52) U.S. Cl.
CPC ........ *A61M 27/006* (2013.01); *A61M 25/007* (2013.01); *A61M 25/04* (2013.01)

(58) Field of Classification Search
CPC .............. A61M 27/006; A61M 25/007; A61M 25/0067; A61M 25/0074
See application file for complete search history.

(56) References Cited

U.S. PATENT DOCUMENTS

| 4,474,569 | A | * | 10/1984 | Newkirk | A61M 25/04 604/247 |
|---|---|---|---|---|---|
| 4,475,898 | A | * | 10/1984 | Brodner | A61M 25/007 604/247 |
| 4,503,569 | A | | 3/1985 | Dotter | |
| 4,595,390 | A | | 6/1986 | Hakim et al. | |
| 5,795,318 | A | | 8/1998 | Wang et al. | |
| 6,159,139 | A | | 12/2000 | Chiu | |
| 6,190,356 | B1 | | 2/2001 | Bersin | |
| 6,371,979 | B1 | | 4/2002 | Beyar et al. | |
| 6,623,508 | B2 | | 9/2003 | Shaw et al. | |
| 6,913,589 | B2 | | 7/2005 | Dextradeur et al. | |
| 7,037,288 | B2 | | 5/2006 | Rosenberg et al. | |
| 8,075,519 | B2 | | 12/2011 | Min et al. | |
| 8,187,222 | B2 | | 5/2012 | Weber et al. | |
| 8,273,056 | B2 | | 9/2012 | Kuracina et al. | |
| 8,366,664 | B2 | | 2/2013 | Magana | |
| 8,439,859 | B2 | | 5/2013 | Pfeffer et al. | |
| 8,475,435 | B2 | | 7/2013 | Bolmsjo et al. | |

(Continued)

*Primary Examiner* — Ariana Zimbouski
(74) *Attorney, Agent, or Firm* — Cohen & Hildebrand, PLLC

(57) ABSTRACT

A self-offsetting implantable valve system including a catheter having an outer perimeter, a free terminating end and an opposite second end. A plurality of holes are defined proximate the free terminating end of the catheter. The system further including a self-offsetting memory component disposed radially about the outer perimeter of a portion of the catheter proximate the free terminating end of the catheter. This self-offsetting memory component is transitionable between a first state subject to application of an externally applied force and a second state free from the externally applied force. While in the first state at least a portion of the self-offsetting memory component having a diameter smaller than that same portion of the self-offsetting memory component while in the second state.

15 Claims, 7 Drawing Sheets

(56) References Cited

U.S. PATENT DOCUMENTS

| | | |
|---|---|---|
| 8,764,711 B2 | 7/2014 | Kuracina et al. |
| 8,777,977 B2 | 7/2014 | Angel |
| 8,827,944 B2 | 9/2014 | Sevrain |
| 9,039,728 B2 | 5/2015 | Angel et al. |
| 9,039,729 B2 | 5/2015 | Angel et al. |
| 2003/0135148 A1* | 7/2003 | Dextradeur ....... A61M 25/0662 604/8 |
| 2007/0016280 A1* | 1/2007 | Yacoby .................. A61F 2/88 623/1.11 |
| 2011/0040371 A1 | 2/2011 | Hanssen et al. |
| 2013/0079856 A1 | 3/2013 | Dabrowiak et al. |
| 2013/0079859 A1 | 3/2013 | Dabrowiak et al. |
| 2014/0121603 A1 | 5/2014 | Min et al. |
| 2014/0249506 A1 | 9/2014 | Laduca |
| 2015/0182377 A1 | 7/2015 | Dabrowiak et al. |
| 2018/0296810 A1* | 10/2018 | Chen .................. A61B 5/031 |

\* cited by examiner

SELF-OFFSETTING IMPLANTABLE CATHETER SYSTEM

BACKGROUND OF THE INVENTION

Field of the Invention

The present invention relates to an implantable catheter system including a catheter having a plurality of pores, holes or openings defined therein and method for using such system. More particularly, the invention relates to an improved catheter system for implantation in the body to drain a bodily fluid, in particular, cerebral spinal fluid (CSF). The present inventive catheter system is specifically designed, following implantation at a target site (e.g., ventricle) in the body, so that over time the catheter automatically remains offset from the ventricle wall, preferably substantially centered in the ventricle. The self-offsetting function of the present inventive catheter system minimizes undesirable obstruction or clogging of pores defined in the catheter that restricts the flow of fluid therethrough.

Description of Related Art

Catheters are used to perform various diagnostic and therapeutic procedures at target sites within the body. One such use for catheters is in treating the condition of hydrocephalus. Hydrocephalus is the accumulation of cerebrospinal fluid (CSF) in the brain, resulting from increased production, or more commonly, pathway obstruction or decreased absorption of the fluid. Cerebrospinal fluid is a clear, colorless fluid that is primarily produced by the choroid plexus and surrounds the brain and spinal cord. CSF constantly circulates through the ventricular system of the brain and is ultimately absorbed into the bloodstream. The CSF aids in the protection of the brain and spinal cord. Specifically, CSF keeps the brain and spinal cord buoyant by acting as a protective cushion or "shock absorber" to prevent injuries to the central nervous system. In addition, the fluid barrier between the CSF and the blood prevents harmful substances from flowing from the capillaries into the CSF.

Hydrocephalus is most often treated by surgically inserting a shunt system that diverts the flow of CSF from the cerebral ventricles or sub-arachnoid spaces to another area of the body (e.g., the right atrium of the heart or the peritoneal cavity) where the CSF may be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or pores positioned along the length of the wall of the ventricular catheter to allow the CSF to enter into the shunt system. To facilitate catheter insertion, a removable rigid stylet, situated within the lumen of the ventricular catheter, is used to direct the catheter toward the desired targeted location. Alternatively, or in addition, blunt tip brain cannulas and peel-away sheaths have been used to aid placement of the catheters.

FIG. 1 is an exemplary illustration of a conventional shunt valve assembly 10 disclosed in U.S. Pat. No. 4,595,390, which is herein incorporated by reference in its entirety. The shunt valve assembly 10 includes one or more one-way shunt valves 12, 14 separated by a pumping chamber 16 that maintain the CSF flowing away from the brain and moderate the pressure or flow rate. Ventricular catheter 18 is connected to the inlet of the valve assembly while a drainage catheter 20 is connected to the outlet of the valve assembly. Ventricular catheter 18 has a plurality of pores, holes or openings defined in its walls proximate its distal end for receiving therethrough the CSF from the ventricle. The diameter of such pores is relatively small (generally, approximately 0.25 mm-approximately 0.50 mm; or approximately 250 micrometers-approximately 500 micrometers). The drainage system using catheters and valves enables the excess CSF within the brain to be evacuated and, thereby, the pressure within the cranium to be maintained within an appropriate range.

This valve assembly may be surgically implanted using well known procedures. During implantation a burr hole is bored through the skull. A stylet is typically utilized as an introducer to properly position the ventricular catheter made of a flexible material (e.g., soft plastic tube) at the desired target site within the brain ventricle. The valve and drainage catheters are fluidly connected to a reservoir disposed proximate the burr hole under the skin. The CSF enters the distal holes of the ventricular catheter and is transported to the abdomen by the drainage catheter. Flow of CSF fluid away from the brain is insured by the one way shunt valve.

Shunting is considered to be a routine neurosurgical procedure, yet implanted hydrocephalus shunts have one of the highest complication rates. At tremendous cost to the health care system ranging in billions of dollars, each year tens of thousands of invasive brain surgeries are required to replace or revise hydrocephalus shunts that have malfunctioned due to mechanical failure. Blockage, occlusion or clogging of the relatively small diameter pores defined in the wall of the catheter, primarily in the ventricular catheter, is the leading cause of mechanical shunt failure and malfunction in hydrocephalus treatment. While there are several ways that the ventricular catheter may become blocked or clogged, obstruction is typically caused by growth of tissue, such as the choroid plexus, around the catheter and into the distal holes or pores. The pores of the ventricular catheter may also be obstructed by debris, bacteria, or blood. Those pores defined in the wall of the catheter that are closest to its free terminating end are particularly susceptible to undesirable blockage due to its close physical proximity to the choroid plexus. To reduce the occurrence of such growth, the catheter is ideally positioned in an area away from the choroid plexus and not in close proximity to the ventricular wall. Despite such efforts, entry of the choroid plexus and other debris into the pores of the catheter may still occur partially or completely obstructing the openings and, in turn, hampering or even prohibiting removal of the catheter if blockage becomes to significant. The location of the catheter is a significant factor. Ideally, the catheter should be positioned in an area away from the choroid plexus and not in close proximity (offset) to the ventricular wall. However, even when optimally positioned in the ventricle, drift over time may cause tissue in growth and obstruction of the drainage holes in the catheter.

It is therefore desirable to develop an improved implantable catheter system for the drainage of CSF or other bodily fluid having an extended operational lifespan by minimizing obstruction and clogging of the pores defined in the wall of the catheter thereby reducing the need for repeated repair and/or replacement of the catheter once implanted in the body.

SUMMARY OF THE INVENTION

An aspect of the present invention is an improved implantable valve assembly including an improve catheter for the drainage of CSF or other bodily fluid having an extended operational lifespan that minimizes obstruction and clogging of the pores defined in the wall of the catheter.

The present inventive catheter is designed with a self-offsetting shape memory feature so that once implanted at a desired target location or site (e.g., a ventricle) in the body over time the catheter automatically remains offsets relative to the ventricle wall.

The present invention is directed to a self-offsetting implantable valve system including a catheter having an outer perimeter, a free terminating end and an opposite second end. A plurality of holes are defined proximate the free terminating; end of the catheter. The system further includes a self-offsetting memory component disposed radially about the outer perimeter of a portion of the catheter proximate the free terminating end of the catheter. This self-offsetting memory component is transitionable between a first state subject to application of an externally applied force and a second state free from the externally applied force. While in the first state at: least: a portion of the self-offsetting memory component having a diameter smaller than that same portion of the self-offsetting memory component while in the second state.

The present invention is further directed to a method for self-offsetting of an implantable catheter system including a catheter having an outer perimeter, a free terminating end and an opposite second end. A plurality of holes are defined proximate the free terminating end of the catheter. The implantable catheter system further includes a self-offsetting memory component disposed radially about the outer perimeter of a portion of the catheter proximate the free terminating, end of the catheter. The self-offsetting memory component is transitionable between a first state subject to, application of an externally applied force and a second state free from the externally applied force. While in the first state at least a portion of the self-offsetting memory component having a diameter smaller or reduce relative to that same portion of the self-offsetting memory component while in the second state. Prior to implantation, the self-offsetting memory component, while in the first state subject to application of the externally applied force, is assembled about at least a portion of the outer perimeter of the catheter proximate the free terminating end of the catheter. While the self-offsetting memory component is subject to the externally applied force in the first state, the first terminating end of the self-offsetting memory component is secured in place relative to the catheter. It is while the self-offsetting memory component is in the first state, the free terminating end of the catheter is advanced to a target site. After passage of a predetermined period of time, complete withdrawal of application of the externally applied force to the self-offsetting memory component permitting the self-offsetting memory component to transition to the second state in which at least a portion of a diameter of the self-offsetting memory component is enlarged relative to that while in the first state and directly physical contact interior walls of a ventricle in which the catheter is implanted. As a result of this direct physical contact between the outer perimeter of the self-offsetting memory component and the interior walls of the ventricle the catheter remains offset in the ventricle over time.

BRIEF DESCRIPTION OF THE DRAWING

The foregoing, and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

By way of illustrative example only, the present invention is Shown and described as an implantable catheter system for the drainage of a bodily fluid, for example, CSF. It is contemplated and within the intended scope of the present invention for the catheter system to be employed for the drainage of other types of bodily fluid.

The terms "proximal"/"proximally" and "distal"/"distally" refer to a direction closer to or away from, respectively, an operator (e.g., surgeon, physician, nurse, technician, user, etc.) who would insert the medical device into the patient, with the opposite tip-end (i.e., distal end or leading end) of the device inserted inside a patient's body. Thus, for example, a "proximal direction" would refer to the direction towards the operator, whereas "distal direction" would refer to the direction away from the operator towards the leading or tip-end of the medical device.

Figure 1:
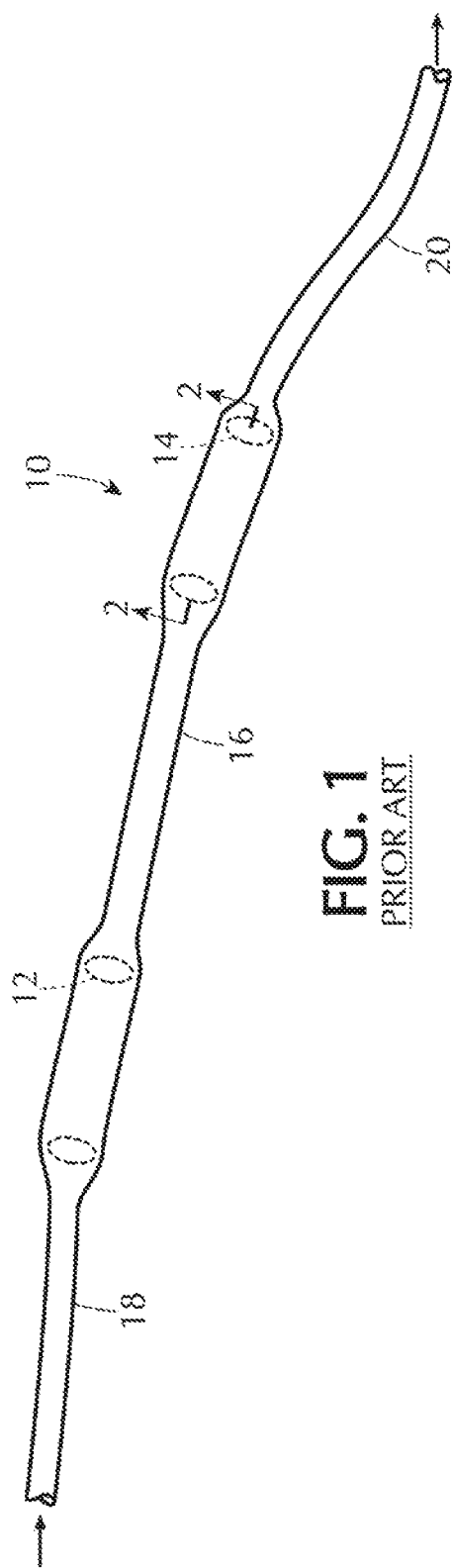
FIG. 1 is a perspective view of a prior art implantable shunt valve system including two shunt valves.
Figure 2A:
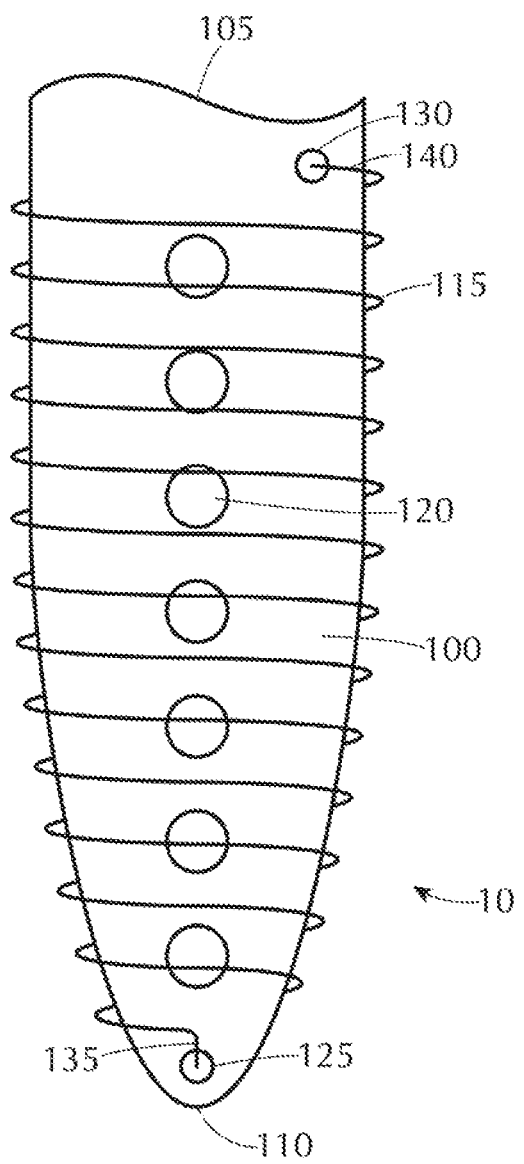
FIG. 2A is a partial side view of a free terminating end portion of an exemplary self-offsetting implantable catheter system prior to implantation in the human body, wherein the present inventive system also includes a self-offsetting memory component in a first state subject to an, externally applied force.
Figure 2B:
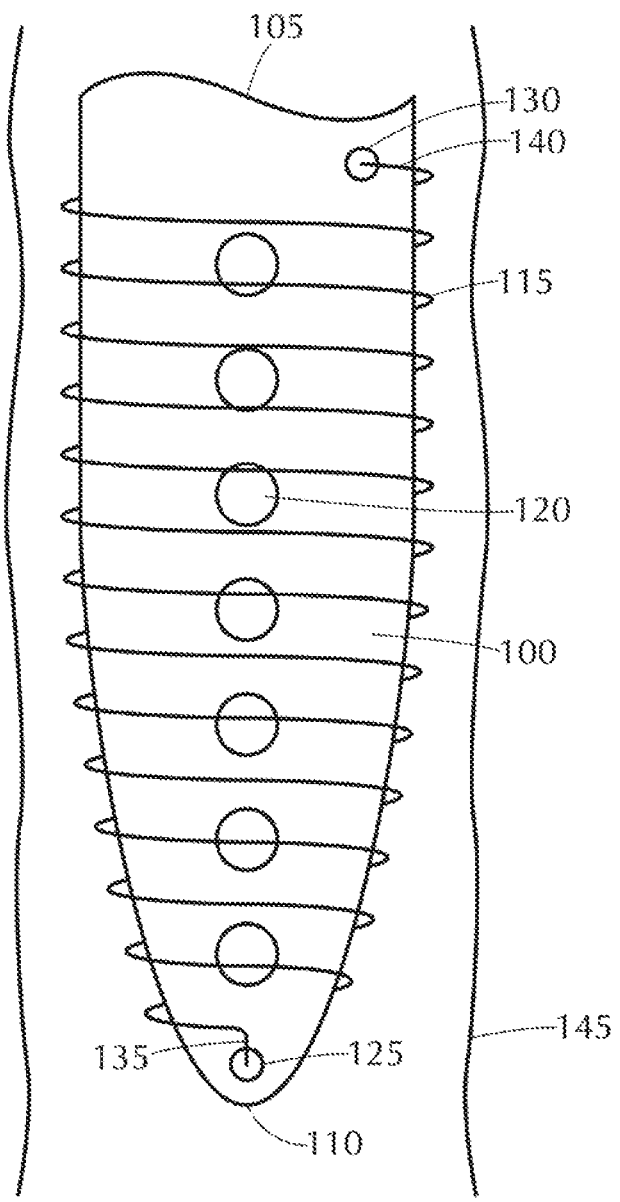
FIG. 2B is a partial side view of the free terminating end portion of the exemplary self-offsetting implantable valve system of FIG. 2A during implantation in a ventricle of the human body with the self-offsetting memory component in the first state subject to the externally applied force.
Figure 2C:
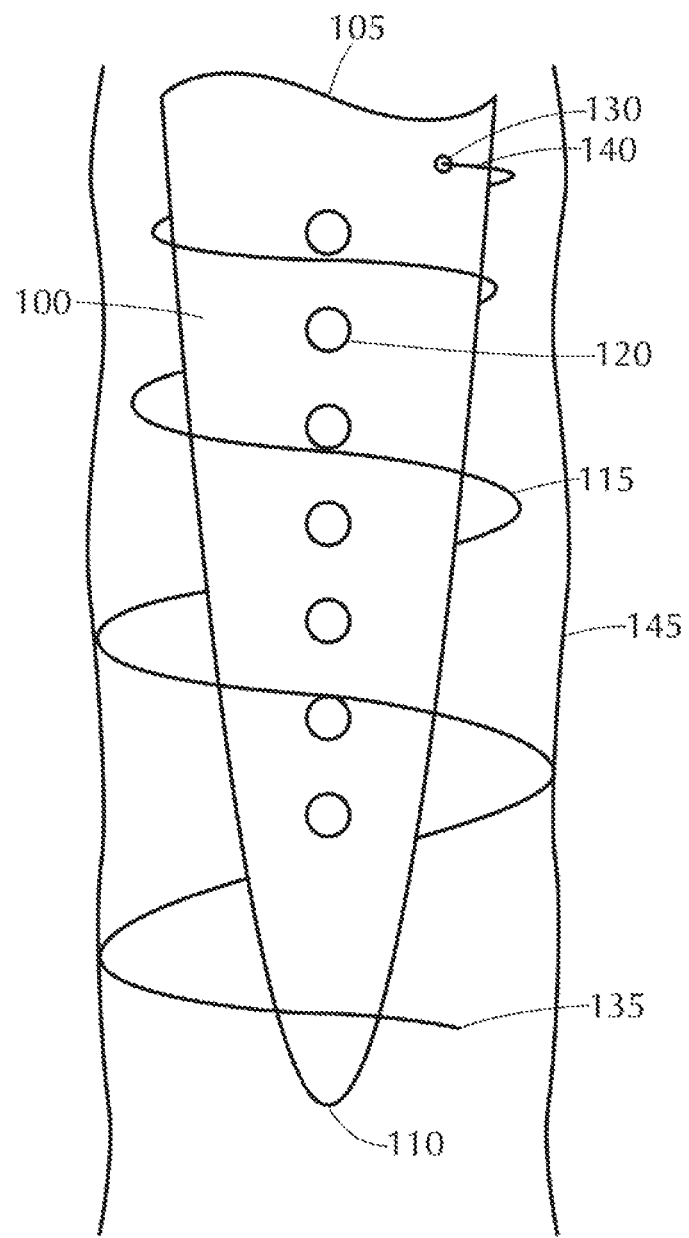
FIG. 2C is a partial side view of the free terminating end portion of the self-offsetting implantable catheter system of FIG. 2A following implantation in the ventricle and after the passage of a predetermined period of time $t_1$ with the self-offsetting memory component in a second state no longer subject to the externally applied force.

The location of the catheter is a significant factor in minimizing undesirable growth of tissue, such as the choroid plexus, around the catheter and into the distal holes or pores defined therein. Ideally, the catheter should be maintained at a position or region that is away from to the choroid plexus and from the ventricular wall, i.e., offset from the ventricle wall, preferably substantially centered within the ventricle. However, even when the catheter during implantation is optimally positioned by being offset from the ventricle wall, preferably substantially centered in the ventricle, drift over time of the position of the catheter in the ventricle may promote, rather than minimize, tissue in growth and obstruction of the drainage holes in the catheter. It is therefore desirable to extend the operational lifespan of the catheter following implantation by maintaining the catheter offset from the ventricle wall, preferably substantially centered within the ventricle, thereby preventing shifting or drift over time towards the choroid plexus and the ventricle wall. Maintaining the implanted drainage catheter so as to be offset from the ventricle wall, preferably substantially centered in the ventricle itself, minimizes growth of tissue around the catheter and into the pores/holes defined in the walls of the catheter, FIG. 2A is a partial side view of a distal end of an exemplary catheter 100 comprising part of a system 10 in accordance with the present invention, prior to implantation at a target site (e.g., in a cerebral ventricle) in a human body or body of an animal. Catheter 100 has a free terminating, end (e.g., distal end) 110 that is not connected to any other component and an opposite second end 105 (e.g., proximal end) connected to other components (e.g., a valve assembly and one or more additional catheters). A plurality of holes, pores or openings 120 are defined in an outer wall of the catheter 100 between its two ends 105, 110. For illustration purposes only, in FIG. 2A seven holes 120 are defined in the outer wall of catheter 100; however, any number of two or more drainage holes are contemplated and within the intended scope of the present invention. Prior to implantation or insertion into the body, a self-offsetting memory component 115, preferably a helix or spiral shape memory coil, is subject to an externally applied force in a radial and/or axial direction (reducing the diameter of the coil) while being wound, preferably in direct physical contact, about the outer perimeter of the catheter 100. The self-offsetting memory component 115 is made of a shape memory material such as a shape memory metal (e.g., Nitinol (NiTi) alloys) and/or a shape memory polymer (e.g., Polytmethyl methacrylate) (PMMA), polyurethanes (PU), poly(eihylene terephthalate) (PET), or polystyrenes (PS)). Other shape memory materials are contemplated and within the intended scope of the present invention so long as when subject to application of an externally applied force the shape memory material is reduced in diameter (i.e., first state), whereupon removal/withdrawal of/free from that same externally applied force the shape Memory material automatically returns to its normal state (e.g. second state) with an enlarged diameter relative to that while in the first state subject to the externally applied force. The self-offsetting memory component 115 having a smaller or reduced diameter while in a state subject to an externally applied force in comparison to that while in a state in which the externally applied force has been withdrawn. While in the second state free from the application of any external force, the diameter of the self-offsetting memory component 115 is enlarged relative to that while in a first state subject to the application of the external force, so that at least a portion of the self-offsetting memory component 115 is in direct physical contact with the inner wall of the cerebral ventricle in which the catheter is to be implanted, as shown in FIG. 2C, Preferably, while in the second state, the self-offsetting memory component has a diameter of at least approximately 2 mm larger than a diameter of the catheter to insure at least a minimum of approximately 1 mm clearance on all sides of the catheter.

During assembly, while subject to the application of the externally applied force, the self-offsetting memory component 115 is secured at least at two points or locations to the catheter 100. Referring to FIG. 2A, preferably, a first terminating end 135 of the self-offsetting memory component 115 is affixed to the catheter 100 at a first securement point 125 disposed proximate the free, terminating end (e.g, distal end) 110 of the catheter 100, and an opposite second terminating end 140 of the self-offsetting memory component 115 is also affixed to the catheter 100 at a second securement point 130 disposed proximate the opposite second end (e.g., proximal end) 105 of the catheter 100. In a preferred embodiment, starting from the first securement point 125 and ending at the second securement point 140, the self-offsetting memory component 115 is at all times in direct physical contact with the outer circumference of the catheter 100 while inure first state subject to the external y applied force. The first securement point 125 is a temporary securement point, while the second securement point 130 is a fixed or permanent securement point. The terms "temporary" versus "fixed or permanent" when describing the respective first and second securement points 125, 135 refer to whether the material used to adhere the two components (self-offsetting memory component 115 and catheter 100) to one another is completely or totally absorbed or degraded in the body over a relatively short predetermined period of time following implantation, or not. That is, the temporary securement point (e.g., the first securement point 125) affixes the first terminating end 135 of the self-offsetting memory component 115 to the catheter 100 proximate the distal end 110 of the catheter 100 using a bioabsorbable, biodegradable or bioresorbable material, i.e., a material that completely or entirely dissolves in the body once its intended purpose has been served (i.e., upon expiration of time $t_1$, preferably with the range of approximately 30 minutes to approximately 25 hrs., after implantation). For instance, the bioabsorbable, biodegradable or bioresorbable material may be a polymer or copolymers made from lactic acid or glycolic acid. The self-offsetting memory component 115 once implanted in the body transitions from the first state to the second state only Once triggered solely by the withdrawal, of the externally applied force applied to the self-offsetting memory component. The term "fixed or permanent" is defined as a material that does not absorb or degrade in the body after being implanted in the body. Hence the second securement point 130 remains affixed between the self-offsetting memory component 115 and the outer perimeter of the catheter 100 at all times during implantation and withdrawal from the body.

By way of illustration only, FIG. 2A shows the exemplary self-offsetting memory component 115 secured at only two points or locations to the catheter 100. It is, however, contemplated and within the intended scope of the present invention for the self-offsetting memory component 115 to be secured to the catheter 100 at more than two locations. In such alternative embodiment with more than two securement points or locations between the self-offsetting memory component 115 and the catheter 100, there is still only a single fixed or permanent securement point. All remaining securement points or locations between the self-offsetting memory component 115 and the catheter 100 in this alternative embodiment are temporary securement points using a bioabsorbable, biodegradable or bioresorbable material that completely and entirely absorbs or degrades in the body after the passage of a predetermined period of time. It is to be noted that when the present inventive system is designed to have more than one temporary securement point wherein the bioabsorbable, biodegradable or bioresorbable material used for each temporary securement point may, but need not necessarily, be the same. For instance, if different bioabsorbable, biodegradable or bioresorbable materials are selected for different temporary securement points, then the rate of complete and total absorption for each material may be varied over time starting with the temporary securement point closest to the distal end 110 of the catheter 100 having the shortest absorption or degradation rate, while the temporary securement point farthest from the distal terminating end 110 (i.e., closest to the proximal end 105) of the catheter 100 having the longest absorption or degradation rate, Referring to FIG. 2C, following implantation of the catheter 100 to a desired target site in the body and the passage of a predetermined period of time $t_1$, the bioabsorbable, biodegradable or bioresorbable material used at the first securement point 125 to secure the first terminating end 135 of the self-offsetting, memory component 115 to the catheter 100 is fully, totally or completely absorbed or degraded (and thus not illustrated in FIG. 2C), In turn, the first terminating end 135 of the self-offsetting memory component 115 is released from the catheter 100 at the temporary securement point 125 thereby withdrawing the externally applied force permitting the self-offsetting memory component 115 to unwind and at least some of its individual spirals to increase in diameter to a fully expanded or second state. When completely unwound in its fully expanded state, the exemplary self-offsetting memory component 115 in FIG. 2C forms an inverted cone with the second terminating end 140 having the smallest diameter remaining adhered to the catheter at the second fixed securement point 130. It is while in such a fully expanded state that there is direct physical contact between enlarged diameter portions of self-offsetting memory component 115 with that of the interior wall of, the cerebral ventricle 145, The enlarged diameter portion of the self-offsetting memory component 115 in direct physical contact with the walls of the cerebral ventricle 145 serve as a supporting structure or cage insuring that the catheter 100 remains offset from the ventricle wall, preferably substantially centrally located in the ventricle 145, over time. Accordingly, a predetermined clearance or distance separation (offset) between the outer perimeter of the catheter 100 and the interior walls of the ventricle 145 is maintained over time. For the entire duration during which the catheter 100 is implanted in the body, the second terminating end 140 of the self-offsetting memory component 115 remains permanently and fixedly attached at all times to the catheter 100 at the second permanent securement point 130.

Catheter 100 is most susceptible to occlusion due to in growth of tissue at the drainage pore/hole 120 that is disposed closest to the free terminating end (e.g., distal end) 110 of the catheter 100. Accordingly, the self-offsetting memory component 115 is preferably positioned along the catheter 100 so that while in an expanded/relaxed/second state (free from the externally applied force) sufficient clearance or distance separation (offset) exists, preferably at least approximately 1 mm, between the wall of the ventricle 145 and that drainage pore/hole 120 disposed closest to the distal end 110 of the catheter 100 to minimize tissue growth in the drainage pore/hole 120. Simultaneously, the self-offsetting memory component. 115 is also made of a material that provides sufficient support, while in a second state free from the externally applied force, to prevent any portion of the catheter 100 from resting on or coming into direct physical contact with the self-offsetting memory component 115 (other than at the second permanent securement point 130).

Rather than the first terminating end 135 of the self-offsetting memory component 115 being temporarily secured directly to the catheter 100 itself as described above, in an alternative configuration the first terminating end 135 of the self-offsetting memory component 115 may be permanently affixed at a securement point 165 to a collar, ring or sleeve 160. Prior to implantation, the collar, ring or sleeve 160 is received on the distal end 110 of the catheter 100. An external force is applied to the self-offsetting memory, component 115 by pulling the collar, ring or sleeve 160 in a longitudinal or axial direction towards the distal end 110 of the catheter 100 thereby reducing in diameter the self-offsetting memory component 115. While subject to this external force, the collar, ring or sleeve 160 is temporarily affixed in place to the outer perimeter of the catheter 100 at a temporary securement point 170 by a bioabsorbable, biodegradable or bioresorbable material. Once the catheter 100 has been implanted and following passage of a predetermined period of time $t_1$ for the bioabsorbable material to be completely absorbed or degraded, the temporary securement point 170 is released thereby withdrawing the externally applied force. No longer subject to the externally applied force the collar, ring or sleeve 160 is permitted to slide over the outer surface of the catheter 100 as the self-offsetting memory component. 115 and retract towards the proximal end 105 of the catheter to its normal/relaxed/second state not subject to an externally applied force). As the collar, ring or sleeve 160 slides towards the proximal end 105 of the catheter 100 a portion of the self-offsetting memory component 115 between the secured first and second terminating ends 135, 140 increases in diameter and comes into direct physical contact with the walls of the ventricle 145. As a result of such direct physical contact, the self-offsetting memory component 115 serves as a supporting structure or cage that maintains over time the catheter 100 disposed therein offset from the ventricle wall, preferably substantially centered within the ventricle 145.

Figure 3A:
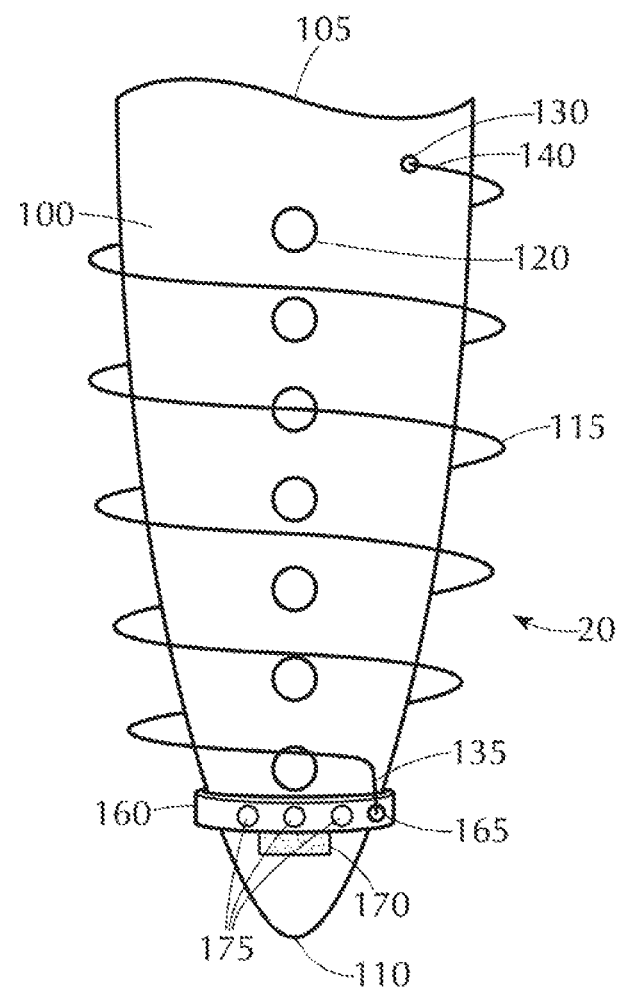
FIG. 3A is a partial side view of the free terminating end portion of a self-offsetting implantable catheter system in a first state subject to an externally applied force prior to implantation in the human body, wherein the present inventive system also includes an alternative self-offsetting, memory component and a collar.
Figure 3B:
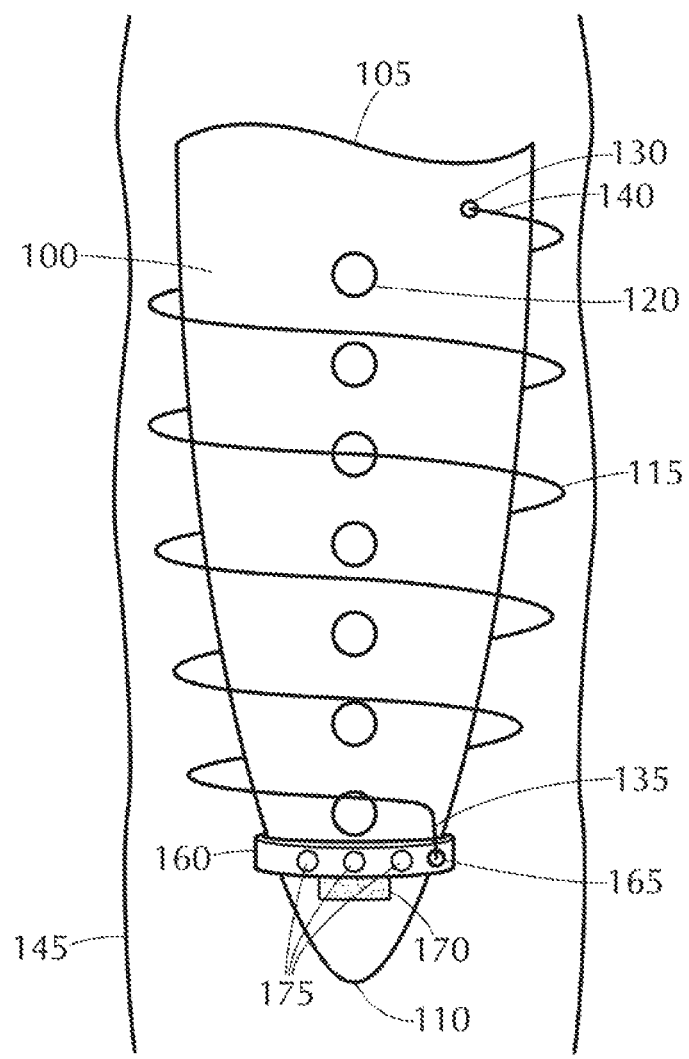
FIG. 3B is the partial side view of the free terminating end portion of the self-offsetting implantable catheter system of FIG. 3A during implantation in a ventricle of the human body with the self-offsetting memory component in the first state subject to the externally applied force.
Figure 3C:
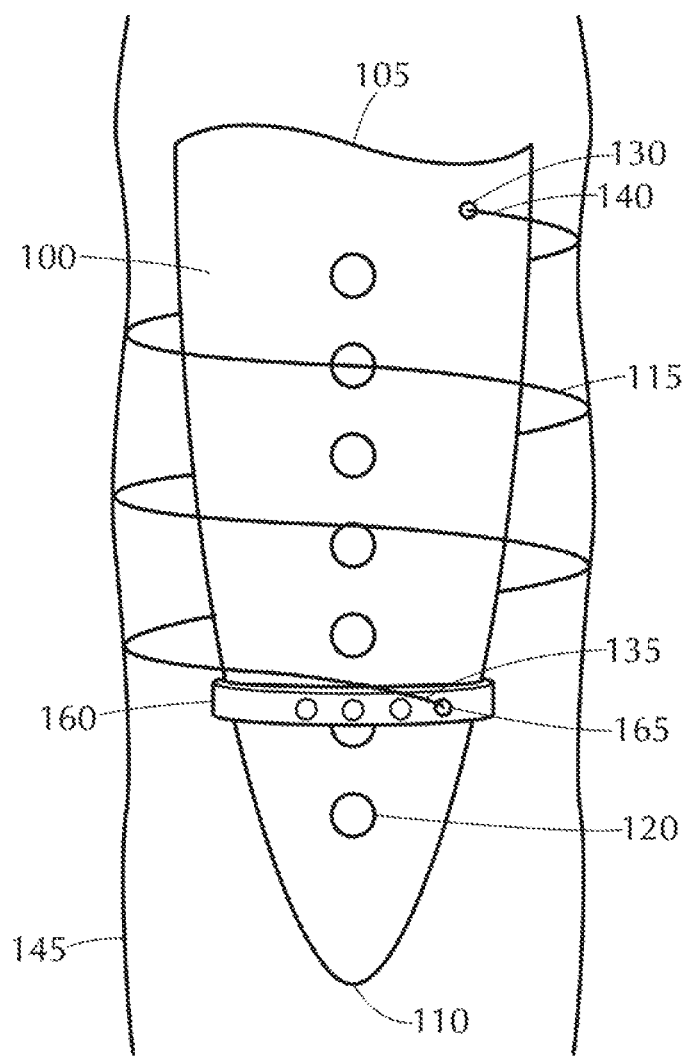
FIG. 3C is a partial side view of the free terminating end portion of the self-offsetting implantable catheter system of FIG. 3A following implantation in the ventricle and after the passage of a predetermined period of time $t_1$ with the self-offsetting memory component in a second state no longer subject to the externally applied force.

One or more holes 175 are shown in FIGS. 3A-3C as being defined in the collar, ring or sleeve 160 so that as the collar slides along the catheter the collar does not occlude or interfere with the passage of fluid through the drainage hole, pores or openings 120 defined in the outer wall of the catheter 100. Furthermore, the diameter of the collar, ring or sleeve 160 is sufficiently large to slide unhindered along the outer perimeter of the catheter 100 starting from the distal end 110 toward the proximal end 105 until the self-offsetting memory component 115 is no longer subject to any externally applied force (i.e., fully relaxed state), Accordingly, the present inventive implantable valve system includes a self-offsetting memory component disposed about an outer perimeter of a catheter proximate the free terminating end (e.g., distal end) of the catheter. During implantation the self-offsetting memory component is subject to an externally applied force (e.g., a force applied in a radial and/or axial direction) whereby the diameter of the self-offsetting memory component is reduced in size to allow sufficient clearance for the catheter and self-offsetting memory component assembled thereon to be advanced through the ventricle to a target site in the body. Following implantation and after passage of a predetermined period of time the externally applied force is withdrawn allowing the self-offsetting memory component to increase in diameter and come into direct physical contact with the interior of the ventricle wall in which the catheter is located. Hence, the self-offsetting memory component serves as a supporting structure or cage to insure that over time the drainage catheter disposed therein is maintained offset relative to the ventricle wall, preferably substantially centrally located in the ventricle, thereby minimizing occurrence with the choroid plexus or physical contact with the ventricle wall. As a result, occlusion or blockage of the distal holes/pores in the drainage catheter as a result of in growth of tissue is minimized or reduced.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended. and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A self-offsetting implantable catheter system, comprising:
    a catheter having an outer perimeter, a free terminating end and an opposite second end; the catheter having a plurality of holes defined proximate the free terminating end of the catheter;
    a self-offsetting memory component disposed radially about the outer perimeter of a portion of the catheter proximate the free terminating end of the catheter; the self-offsetting memory component being a helical or spiral memory coil; the self-offsetting memory component being transitionable between: (i) a first state subject to application of an externally applied force prior to and during implantation wherein the self-offsetting memory component is secured relative to the catheter; and (ii) a second state free from the externally applied force; wherein while in the first state at least a portion of the self-offsetting memory component having a diameter smaller than that same portion of the self-offsetting memory component while in the second state.

2. The self-offsetting implantable catheter system according to claim 1, the self-offsetting memory component being secured about the at least a portion of the outer perimeter of the catheter while in the first state subject to application of the externally applied force; wherein the externally applied force is a radial force and an axial force.

3. The self-offsetting implantable catheter system according to claim 1, wherein the self-offsetting memory component has two terminating ends including a first terminating end of the self-offsetting memory component being disposed proximate the free terminating end of the catheter and an opposite second terminating end of the self-offsetting memory component being disposed proximate the opposite second end of the catheter.

4. The self-offsetting implantable catheter system according to claim 3, wherein the first terminating end of the self-offsetting memory component is affixed directly to the outer perimeter of the catheter at a securement point via a bioabsorbable material or biodegradable material fully absorbable or degradable over a predetermined period of time; and the second terminating end of the self-offsetting memory component is permanently affixed directly to the catheter.

5. A self-offsetting implantable catheter system, comprising:
    a catheter having an outer perimeter a free terminating end and an opposite second end; the catheter having a plurality of holes defined proximate the free terminating end of the catheter;
    a self-offsetting memory component disposed radially about the outer perimeter of a portion of the catheter proximate the free terminating end of the catheter; the self-offsetting memory component being a helical or spiral memory coil; the self-offsetting memory component being transitionable between a first state subject to application of an externally applied force and a second state free from the externally applied force; wherein while in the first state at least a portion of the self-offsetting memory component having a diameter smaller than that same portion of the self-offsetting memory component while in the second state;
    wherein the self-offsetting memory component has two terminating ends including a first terminating end of the self-offsetting memory component being disposed proximate the free terminating end of the catheter and an opposite second terminating end of the self-offsetting memory component being disposed proximate the opposite second end of the catheter;
    wherein the first terminating end of the self-offsetting memory component is permanently secured to a collar slidably receiveable on the outer perimeter of the free terminating end of the catheter; wherein the collar is affixed directly to the outer perimeter of the catheter via a bioabsorbable material or biodegradable material fully absorbable or degradable over a predetermined period of time; the first terminating end of the self-offsetting memory component is not directly affixed to the outer perimeter of the catheter; and the second terminating end of the self-offsetting memory component is permanently affixed directly to the outer perimeter of the catheter.

6. A method for self-offsetting of an implantable catheter system including a catheter having an outer perimeter, a free terminating end and an opposite second end; the catheter having a plurality of holes defined proximate the free terminating end of the catheter; the implantable catheter system further including a self-offsetting memory component disposed radially about the outer perimeter of a portion of the catheter proximate the free terminating end of the catheter; the self-offsetting memory component being a helical or spiral memory coil; the self-offsetting memory component transitionable between a first state subject to application of an externally applied force and a second state free from the externally applied force; wherein while in the first state at least a portion of the self-offsetting memory component having a diameter smaller than that same portion of the self-offsetting memory component while in the second state; the method comprising the steps of:
    prior to implantation, assembling the self-offsetting memory component, while in the first state subject to application of the externally applied force, about at least a portion of the outer perimeter of the catheter proximate the free terminating end of the catheter;

while the self-offsetting memory component is subject to the externally applied force in the first state prior to implantation, securing in place the self-offsetting memory component relative to the catheter;

during implantation, while the self-offsetting memory component is in the first state subject to application of the externally applied force, advancing the free terminating end of the catheter to a target site;

once positioned at the target site and after passage of a predetermined period of time, complete withdrawal of application of the externally applied force to the self-offsetting memory component and transitioning the self-offsetting memory component to the second state in which at least a portion of a diameter of the self-offsetting memory component is enlarged relative to that while in the first state to directly physically contact interior walls of a ventricle in which the catheter is implanted so as to maintain over time catheter offset relative to the interior walls of the ventricle.

7. The method according to claim 6, wherein the self-offsetting memory component has two terminating ends including a first terminating end of the self-offsetting memory component being disposed proximate the free terminating end of the catheter and an opposite second terminating end of the self-offsetting memory component being disposed proximate the opposite second end of the catheter.

8. The method according to claim 7, wherein the securing step comprises adhering the first terminating end of the self-offsetting memory component directly to the catheter using a bioabsorbable or biodegradable material at a securement point.

9. The method according to claim 8, wherein the step of complete withdrawal of application of the externally applied force occurs after absorption or degradation of the bioabsorbable or biodegradable material at the securement point over a predetermined period of time after implantation.

10. A method for self-offsetting of an implantable catheter system including a catheter having an outer perimeter, a free terminating end and an opposite second end; the catheter having a plurality of holes defined proximate the free terminating end of the catheter; the implantable catheter system further including a self-offsetting memory component disposed radially about the outer perimeter of a portion of the catheter proximate the free terminating end of the catheter; the self-offsetting memory component being a helical or spiral memory coil; the self-offsetting memory component transitionable between a first state subject to application of an externally applied force and a second state free from the externally applied force; wherein while in the first state at least a portion of the self-offsetting memory component having a diameter smaller than that same portion of the self-offsetting memory component while in the second state; the method comprising the steps of:

prior to implantation, assembling the self-offsetting memory component, while in the first state subject to application of the externally applied force, about at least a portion of the outer perimeter of the catheter proximate the free terminating end of the catheter;

while the self-offsetting memory component is subject to the externally applied force in the first state, securing in place the self-offsetting memory component relative to the catheter;

while the self-offsetting memory component is in the first state, advancing the free terminating end of the catheter to a target site;

once positioned at the target site and after passage of a predetermined period of time, complete withdrawal of application of the externally applied force to the self-offsetting memory component and transitioning the self-offsetting memory component to the second state in which at least a portion of a diameter of the self-offsetting memory component is enlarged relative to that while in the first state to directly physically contact interior walls of a ventricle in which the catheter is implanted so as to maintain over time catheter offset relative to the interior walls of the ventricle;

wherein the self-offsetting memory component has two terminating ends including a first terminating end of the self-offsetting memory component being disposed proximate the free terminating end of the catheter and an opposite second terminating end of the self-offsetting memory component being disposed proximate the opposite second end of the catheter;

wherein the securing step comprises permanently adhering the first terminating end of the self-offsetting memory component directly to a collar slidably receiveable on the outer perimeter of the free terminating end of the catheter; wherein the collar is affixed directly to the outer perimeter of the catheter via a bioabsorbable material or biodegradable material fully absorbable or degradable over a predetermined period of time after implantation; the first terminating end of the self-offsetting memory component is not directly affixed to the outer perimeter of the catheter; and the second terminating end of the self-offsetting memory component is permanently affixed directly to the outer perimeter of the catheter.

11. The method according to claim 10, wherein the step of complete withdrawal of application of the externally applied force occurs after absorption or degradation of the bioabsorbable or biodegradable material.

12. The method according to claim 6, wherein the externally applied force is a radial force and an axial force.

13. A method for self-offsetting of an implantable catheter system including a catheter having an outer perimeter, a free terminating end and an opposite second end; the catheter having a plurality of holes defined proximate the free terminating end of the catheter; the implantable catheter system further including a self-offsetting memory component disposed radially about the outer perimeter of a portion of the catheter proximate the free terminating end of the catheter; the self-offsetting memory component being a helical or spiral memory coil; the self-offsetting memory component transitionable between a first state subject to application of an externally applied force and a second state free from the externally applied force; wherein while in the first state at least a portion of the self-offsetting memory component having a diameter smaller than that same portion of the self-offsetting memory component while in the second state; the method comprising the steps of:

prior to implantation, assembling the self-offsetting memory component, while in the first state subject to application of the externally applied force, about at least a portion of the outer perimeter of the catheter proximate the free terminating end of the catheter; the self-offsetting memory component being in the first state subject to application of the externally applied force during implantation;

while the self-offsetting memory component is subject to the externally applied force in the first state, securing in place the self-offsetting memory component relative to the catheter;

while the self-offsetting memory component is in the first state, advancing the free terminating end of the catheter to a target site;

once positioned at the target site and after passage of a predetermined period of time, complete withdrawal of application of the externally applied force to the self-offsetting memory component and transitioning the self-offsetting memory component to the second state in which at least a portion of a diameter of the self-offsetting memory component is enlarged relative to that while in the first state to directly physically contact interior walls of a ventricle in which the catheter is implanted so as to maintain over time catheter offset relative to the interior walls of the ventricle; and wherein during the advancing step, the self-offsetting memory component is subject to the externally applied force whereby a diameter of the self-offsetting memory component is reduced in size to allow sufficient clearance for the catheter and the self-offsetting memory component assembled thereon to be advanced through the ventricle to the target site.

14. A self-offsetting implantable catheter system comprising:

a catheter having an outer perimeter, a free terminating end and an opposite second end; the catheter having a plurality of holes defined proximate the free terminating end of the catheter; and a self-offsetting memory component disposed radially about the outer perimeter of a portion of the catheter proximate the free terminating end of the catheter; the self-offsetting memory component being a helical or spiral memory coil; the self-offsetting memory component being transitionable between: (i) a first state subject to application of an externally applied force prior to and during implantation; and (ii) a second state free from the externally applied force; wherein while in the first state at least a portion of the self-offsetting memory component having a diameter smaller than that same portion of the self-offsetting memory component while in the second state;

the self-offsetting memory component having a wound configuration radially about the outer perimeter of the portion of the catheter proximate the free terminating end of the catheter while in the first state subject to application of an externally applied force prior to and during implantation.

15. A method for self-offsetting of an implantable catheter system including a catheter having an outer perimeter, a free terminating end and an opposite second end; the catheter having a plurality of holes defined proximate the free terminating end of the catheter; the implantable catheter system further including a self-offsetting memory component disposed radially about the outer perimeter of a portion of the catheter proximate the free terminating end of the catheter; the self-offsetting memory component being a helical or spiral memory coil; the self-offsetting memory component transitionable between a first state subject to application of an externally applied force and a second state free from the externally applied force; wherein while in the first state at least a portion of the self-offsetting memory component having a diameter smaller than that same portion of the self-offsetting memory component while in the second state; the method comprising the steps of:

prior to implantation, assembling the self-offsetting memory component, while in the first state subject to application of the externally applied force, about at least a portion of the outer perimeter of the catheter proximate the free terminating end of the catheter; the self-offsetting memory component being in the first state subject to application of the externally applied force during implantation;

while the self-offsetting memory component is subject to the externally applied force in the first state, securing in place the self-offsetting memory component relative to the catheter;

while the self-offsetting memory component is in the first state, advancing the free terminating end of the catheter to a target site;

once positioned at the target site and after passage of a predetermined period of time, complete withdrawal of application of the externally applied force to the self-offsetting memory component and transitioning the self-offsetting memory component to the second state in which at least a portion of a diameter of the self-offsetting memory component is enlarged relative to that while in the first state to directly physically contact interior walls of a ventricle in which the catheter is implanted so as to maintain over time catheter offset relative to the interior walls of the ventricle; and prior to implantation, the assembling step comprising winding the self-offsetting memory component, while in the first state subject to application of the externally applied force, about at least a portion of the outer perimeter of the catheter proximate the free terminating end of the catheter.

* * * * *